(12) United States Patent
Gaudreau et al.

(10) Patent No.: US 8,163,328 B2
(45) Date of Patent: Apr. 24, 2012

(54) COMPOSITIONS FOR MARKING OBJECTS WITH DNA AND METHODS FOR MARKING AND LINKING AN OBJECT TO ITS OWNER

(75) Inventors: Marc Gaudreau, Ottawa (CA); Faisal Ibrahim, Gatineau (CA)

(73) Assignee: Forensink Corporation, Inc., Ottawa, Ontario (CA)

( * ) Notice: Subject to any disclaimer, the term of this patent is extended or adjusted under 35 U.S.C. 154(b) by 499 days.

(21) Appl. No.: 11/719,448

(22) PCT Filed: Nov. 17, 2005

(86) PCT No.: PCT/CA2005/001752
§ 371 (c)(1),
(2), (4) Date: Aug. 2, 2007

(87) PCT Pub. No.: WO2006/053435
PCT Pub. Date: May 26, 2006

(65) Prior Publication Data
US 2009/0253127 A1 Oct. 8, 2009

Related U.S. Application Data

(60) Provisional application No. 60/628,115, filed on Nov. 17, 2004.

(51) Int. Cl.
| | |
|---|---|
| *B41M 3/14* | (2006.01) |
| *B44F 1/12* | (2006.01) |
| *B05B 5/00* | (2006.01) |
| *D06L 3/12* | (2006.01) |
| *G01D 11/00* | (2006.01) |
| *G01D 13/00* | (2006.01) |
| *G01N 31/22* | (2006.01) |
| *C12Q 1/68* | (2006.01) |
| *C07H 21/02* | (2006.01) |
| *C07H 21/04* | (2006.01) |

(52) U.S. Cl. .............. 427/7; 427/157; 116/200; 435/6.1
(58) Field of Classification Search .................. None
See application file for complete search history.

(56) References Cited

U.S. PATENT DOCUMENTS

| | | | |
|---|---|---|---|
| 3,261,796 A | 7/1966 | Simms | |
| 5,139,812 A | 8/1992 | Lebacq | |
| 5,474,931 A * | 12/1995 | DiSorbo et al. | ............... 435/407 |
| 6,258,581 B1 * | 7/2001 | Okino et al. | .................. 435/195 |
| 2003/0166180 A1* | 9/2003 | Bramucci et al. | ............. 435/146 |
| 2004/0219287 A1 | 11/2004 | Regan et al. | |

FOREIGN PATENT DOCUMENTS

| | | |
|---|---|---|
| CA | 2 341 444 | 3/2000 |
| CA | 2 415 226 | 4/2003 |
| WO | WO 00/26021 | 5/2000 |

OTHER PUBLICATIONS

International Search Report of PCT/CA2005/001752 mailed Mar. 7, 2006.
Phillips Jones (2004) "DNA Forensics: From RFLP to PCR-STR and Beyond" Forensics Magazine (text can be found at http://forensicmag.com/articles/0904dna.asp?pid=17&articleText=0904dna).
Van Schie & Wilson (1997) "Saliva: a convenient source of DNA for analysis of bi-allelic polymorphisms of Fcy receptor IIA (CD32) and Fcy receptor IIIB (CD16)" J. Immunol. Methods 208:91-101.
Terasaki et al. (1998) "Saliva as DNA Source for HLA Typing" Human Immunol. 59:597-598.

* cited by examiner

*Primary Examiner* — Teresa E Strzelecka
(74) *Attorney, Agent, or Firm* — Suzannah K. Sundby; Smith, Gambrell & Russell, LLP (57) ABSTRACT

The invention can be summarized as follows. There is provided one or more DNA coating compositions that comprise one or more polymer compounds, water, and optionally one or more non-water polar solvents. The DNA coating composition may also comprise DNA. Also provided are methods and kits for marking objects with a DNA coating composition comprising DNA.

20 Claims, 2 Drawing Sheets

COMPOSITIONS FOR MARKING OBJECTS WITH DNA AND METHODS FOR MARKING AND LINKING AN OBJECT TO ITS OWNER

This application claims the benefit of U.S. patent application Ser. No. 60/628,115, filed 17 Nov. 2004, which is herein incorporated by reference in its entirety.

The present invention relates to compositions and methods for marking objects for identification.

BACKGROUND OF THE INVENTION

Lost or stolen possessions that are found or recovered by police or a third party often cannot be returned to their rightful owners unless the owners have notified the police that a possession is missing. In cases where a possession may be of great value and the owner is sure it has been stolen, the police may be notified. However, an owner of a possession is unlikely to notify the police if a possession is lost, misplaced or if the owner does not know that the possession has been lost or stolen.

It is also known in the art that ownership claims in respect of lost or stolen possessions that are recovered can be difficult as the owner often must prove that he or she is the rightful owner of the recovered object. In some cases, receipts must be produced that describe the recovered article, or serial numbers must be provided in advance to establish ownership. In many cases, the rightful owner of an article may not keep receipts or serial numbers of the articles that he or she purchases. Thus, there is a need in the art for unique marking compositions that can be used to mark personal property including for example, articles of value. Further, there is a need in the art for novel methods of marking objects of personal property to facilitate claims of ownership and return should the personal property be stolen or lost and subsequently recovered. Further, there is a need in the art for a searchable electronic database system to identify, list and describe objects that have been lost or stolen and for police to return recovered possessions to their rightful owners.

It is an object of the invention to overcome disadvantages of the prior art.

The above object(s) is met by the combinations of features of the main claims, the sub-claims disclose further advantageous embodiments of the invention.

SUMMARY OF THE INVENTION

The present invention relates to compositions and methods for marking objects for identification.

According to the present invention there is provided a DNA coating composition comprising,
 a) one or more polymer compounds;
 b) water,
 and optionally,
 c) one or more non-water polar solvents.

The present invention also provides a DNA coating composition as defined above wherein the one or more polymer compounds comprises polyurethane or acrylic polymer and the one or more polar solvents comprises methanol.

The present invention further contemplates a DNA coating composition as defined above wherein the composition comprises one or more dispersants, curing agents, catalysts, preservatives, enzyme inhibitors, thickeners, fillers, biocidal agents, buffering agents, luminescent compounds or dyes, antioxidants and/or reducing agents, detergents and/or denaturing agents, salts, light absorbing compounds, chelating agents, corrosion inhibitors, film forming components, plasticizers, adhesion promoters or a combination thereof.

The present invention further contemplates a DNA coating composition as defined above wherein the DNA coating composition further comprising a DNA nucleotide sequence.

The present invention further contemplates a DNA coating composition as defined above wherein the composition further comprises silica.

The present invention further contemplates a DNA coating composition as defined above wherein the composition comprises about 62% (w/w) deionized water, about 20% (w/w) methanol, about 12% (w/w) polyurethane, about 2.5% (w/w) p-aminobenzoic acid, about 2% (w/w) manganese chloride from 1M stock solution, about 0.5% (w/w) fumed silica, about 0.5% (w/w) citric acid, about 0.1% (w/w) 2,5-thiophenediylbis(5ter-butyl-1,3-benzoxazole), about 0.1% (w/w) EDTA from 0.1 M solution, about 0.05% (w/w) sodium azide and about 0.01% (w/w) Dowicil 75.

Also provided by the present invention is a method of treating an object with a DNA coating composition comprising,
 a) selecting a DNA coating composition;
 b) obtaining DNA from a subject;
 c) adding the DNA from a subject to the DNA coating composition to produce a DNA coating composition that comprises DNA to the object.

Also provided by the present invention is a method of processing an object treated with a DNA coating composition comprising,
 a) obtaining an object treated with a DNA coating composition that comprises DNA;
 b) treating the DNA coating composition to remove DNA contained in the DNA coating composition;
 c) optionally purifying the DNA;
 d) subjecting the DNA to an amplification process to produce amplified DNA and analyzing the amplified DNA.

The method as defined above may further comprise additional steps, for example, but not limited to
 a) searching a database for objects marked with a DNA coating composition or items recovered or found that have been treated with the DNA coating composition;
 b) entering information regarding one or more objects treated with the DNA coating composition into a database, or
 c) a combination thereof.

The present invention also provides a kit comprising a DNA coating composition. The kit may also comprise one or more implements for obtaining DNA from a biological fluid or tissue of a subject, instructions for obtaining DNA from the subject, one or more sample DNA archive pouches, a DNA coating composition applicator, instructions for marking objects, one or more forms to list marked items, a log-on ID, password or unique identifier code, one or more containers, instructions for searching a website, instructions for submitting information to a website about objects that have been marked, or a combination thereof.

The present invention also contemplates a system for linking an object to an owner comprising,
 a database comprising information concerning an item owned by a subject, information concerning an item found or recovered, or a combination thereof, and;
 a DNA coating composition or a kit comprising the DNA coating composition.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein.

DESCRIPTION OF PREFERRED EMBODIMENT

The following description is of a preferred embodiment by way of example only and without limitation to the combination of features necessary for carrying the invention into effect.

DNA Coating Compositions:

According to an aspect of the present invention, there is provided a DNA coating composition comprising, a) one or more polymer compounds;
b) water;
and optionally,
c) one or more non-water polar solvents.

The DNA coating composition comprises one or more polymer compounds. Examples of polymer compounds include, but are not limited to polyurethanes; polyesters; polyvinyl chloride (PVC); polyvinyl acetate (PVA); polyamides, polyolefins for example, but not limited to polyethylene and polypropylene; polyesters including, but not limited to polyethylene terephthalate, polybutylene terephthalate, and the like; polyamides; polysulfones; polyimides; polyether imides; polyether glycols; polyether ketones; polyether ether ketones; polybutadiene; polyacrylates for example, but not limited to polymethylmethacrylate, methyl methacrylate-polyimide, and copolymers thereof; polyacrylonitrile; polyacetals; polycarbonates; polyurethanes, for example, but not limited to an isocyanate component and a polyol blend component; polyphenylene ethers; ethylene-vinyl acetate copolymers; ethylene-tetrafluoroethylene copolymers; aromatic polyesters; polyvinyl fluoride; polyvinylidene fluoride; polyvinylidene chloride; nitrocellulose polymers, or a combination thereof. Preferably, the polymer compound comprises one or more of polyurethanes, polyesters, polyvinylchloride, polyvinyl acetate, polyamides or a combination thereof. In a specific embodiment, the polymer compound comprises polyurethane or acrylic polymer.

The one or more polymer compounds may also be provided by way of a composition comprising one or more polymer compounds. It is also contemplated that the one or more polymer compounds may be provided as an enamel or enamel composition that is capable of hardening following application to an object or the like.

The one or more polymer compounds may be present in a range from about 5% to about 60% by weight, preferably about 10% to about 50% by weight, more preferably 20% to about 40% by weight. In an embodiment of the present invention, the polymer compound is polyurethane and is present in the composition in an amount of about 12% by weight. In separate embodiments of the present invention, the polymer compound is present in an amount of about 5%, 7%, 9%, 10%, 12%, 15%, 17%, 20%, 22%, 25%, 27%, 30%, 32%, 34%, 35%, 37%, 40%, 42%, 45%, 48%, 50%, 55%, or 60% by weight. Alternatively, the polymer may be present in a range defined by any two of the values listed above.

The DNA coating composition may further comprise one or more additional components, for example, but not limited to dispersants, curing agents, catalysts, preservatives, enzyme inhibitors, thickeners, fillers, biocidal agents, buffering agents, luminescent compounds or dyes, antioxidants and/or reducing agents, detergents and/or denaturing agents, salts, light absorbing compounds, chelating agents, corrosion inhibitors, film forming components, for example, but not limited to nitrocellulose, cellulose acetate butyrate, or a combination of one or both of these cellulosic compounds, plasticizers, adhesion promoters or a combination thereof. The DNA coating composition may also comprise a nucleotide sequence, for example, but not limited to DNA, RNA or both from a subject. Alternatively, the nucleotide sequence may be a synthetic sequence.

It is to be understood that a component may be characterized as belonging to one or more categories as defined above. For example, a component listed herein as a detergent may also be an enzyme inhibitor and a biocidal agent. Inclusion of a component in a particular category does not preclude that component from also being included in one or more additional categories.

The DNA coating composition may optionally comprise one or more non water polar solvents, preferably exhibiting a dielectric constant above about 20 when measured at around 25° C. Examples of solvents that may be employed in the present invention include, but are not limited to acetone, aliphatic or aromatic alcohols such as, but not limited to ethanol, methanol, propanol, isopropanol, butenol, t-butenol or a combination thereof. In a preferred embodiment, the boiling point of the one or more polar solvents is each independently below about 100° C. Other polar solvents, as would be known in the art are also contemplated by the present invention. Preferably the one or more solvents are high grade, meaning that the one or more solvents comprise low amounts of other components. For example, the purity of the solvent is preferably greater than about 95%, more preferably greater than about 98%, more preferably greater than about 99%, still more preferably greater than about 99.9% pure.

Compositions that comprise once or more solvents that exhibit relatively low boiling points, for example, below about 100° C. may accelerate the drying time of the coating as compared to substantially identical coating compositions, comprising solvents that exhibit relatively higher points. Preferably, each of the one or more solvents has a boiling point below about 100° C., preferably below about 90° C., more preferably below about 80° C.

The one or more polar solvents may be present in the DNA coating composition in an amount of about 0% to 70% by weight, more preferably about 5% to about 60% by weight. However, the one or more polar solvents may be present in a range of about 5% to about 40%, about 10% to about 50%, about 20% to about 60% or about 30% to about 70%. In specific embodiments, the one or more polar solvents may be present in a total amount of about 0%, 5%, 10%, 15%, 20%, 25%, 30%, 35%, 40%, 45%, 50%, 55%, 60%, 65%, 70% by weight, or any range defined by any two of the values listed above. In an embodiment of the present invention, the polar solvent is methanol and it is present in the composition in an amount of about 15% to 20% by weight.

It is generally preferred that substantial amounts of non-polar solvents comprising a dielectric constant below about 20 are not employed in the DNA coating composition of the present invention. For example, it is preferable to avoid the use of solvents such as, but not limited to ethyl acetate, methyl ethyl ketone and toluene.

Water comprises the remaining portion of the DNA coating composition. The water that is employed in the DNA coating composition is preferably substantially pure, for example free of particulates, bacteria, and metals as such components may affect the stability of the DNA, in the coating composition. In an embodiment of the present invention, which is not meant to be limiting in any manner, the water employed is distilled, deionised, filtered, for example, but not limited to sterile filtered, or a combination thereof.

The DNA coating composition may further comprise silica, for example, but not limited to fumed silica. Without wishing to be bound by theory, or limiting in any manner, the silica may act as a dispersant to maintain components such as DNA suspended in the composition. In this manner, and again without wishing to be bound by theory, the silica may also act as a binding agent for DNA or nucleic acids. Preferably, the dispersant is a fumed silica such as, but not limited to CAB-O-SIL (Cabot corp.), AEROSIL (DOW Chemical corp.), or a combination thereof. Combinations of silicas, and fumed silicas are also contemplated herein. Silica, preferably fumed silica may be present in the composition in an amount of about 0.005% to about 5% by weight, for example 0.01%, 0.05%, 0.1%, 0.5%, 1%, 2%, 3%, 4%, 5% or a range defined by any two of the values listed above. In an embodiment of the present invention, the silica is fumed silica and is present in an amount of about 0.5% by weight. In an alternate embodiment, which is not meant to be limiting in any manner, the silica is provided by silica microbeads comprising a diameter less than about 50μ, preferably less than about 40μ, preferably less than about 30μ preferably less than about 20μ, preferably less than about 10μ, more preferably about 5μ or less in diameter.

The DNA coating composition may comprise one or more light absorbing compounds, for example, but not limited to UV light absorbing compounds. Examples of compounds that absorb ultraviolet light include, but are not limited to p-aminobenzoic acid, oxyethylene, p-aminobenzoate, 2-ethylhexyl p-dimethylaminobenzoate, ethyl N-oxypropylene p-aminobenzoate, glycerol p-aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammunium)-benzyliden-bornan-2-one methylsulfate, benzophenone, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4'dimethoxybenzophenone, 2-hydroxy-4-n-octoxybenzophenone, 2-hydroxy-4-methoxy-4'-methoxybenzophenone, 2,4-bis{[4-(2-ethyl-hexyloxy)]-2-hydroxy]-phenyl}-6-(4-methoxy-phenyl)-1,3,5-triazine ("TINOSORB S" marketed by Ciba),ferulic acid, gamma-orizanol, or a combination thereof. Preferably the UV absorbing compounds are present in the DNA coating composition in an amount from about 0.001% to about 3% by weight. Further, it is contemplated that the UV absorbing compound may be present in an amount of about 0.001%, 0.005%, 0.01%, 0.05%, 0.1%, 0.5%, 1%, 2% by weight or any range defined by two of the values. In a specific embodiment of the present invention, the UV absorbing compound is p-aminobenzoic acid and it is present in an amount of about 2.5% by weight.

The DNA coating composition may comprise one or more enzyme inhibitors, for example, but not limited to, deoxyribonuclease inhibitors, ribonuclease inhibitors, or both. Enzyme inhibitors may also include salts or detergents that are present in an amount sufficient to inhibit one or more enzymes such as deoxyribonucleases, ribonucleases or both. Without wishing to be limiting in any manner, an example of a salt that may be considered an enzyme inhibitor is manganese chloride. An example of a detergent that may be considered an enzyme inhibitor is dodecyl sulfate, for example, but not limited sodium dodecyl sulfate (SDS). A salt or detergent may be considered an enzyme inhibitor if it is capable of reducing the activity of an enzyme, preferably one or more deoxyribonucleases, ribonucleases or both by at least about 10%, more preferably at least about 20%, more preferably at least about 50%, more preferably at least about 80%, more preferably at least about 90%, more preferably at least about 95%, more preferably at least about 99%, or greater when used in a defined amount. It is to be understood that the amount of salt or detergent employed in the DNA coating composition may be adjusted so that that the composition exhibits enzyme inhibition. A variety of enzyme assays are known in the art and any assay may be used to determine if a salt or detergent may be employed as a enzyme inhibitor, and if so the concentration range that may be employed in the DNA coating composition. In an embodiment of the present invention, the composition comprises manganese chloride as an enzyme inhibitor in an amount of up to about 2% by weight of the composition. In a specific embodiment, which is not meant to be limiting in any manner, the composition comprises 2% by weight of a 1M manganese chloride stock solution.

The DNA coating composition may also comprise one or more salts, for example, but not limited to stabilize the charge on DNA contained in the solution.

The DNA coating composition may comprise one or more reducing agents, for example, but not limited to ascorbic acid, dithionite, erythiorbate, N-acetylcysteine, cysteine, glutathione, dithiothreitol, 2-mercaptoethanol, dierythritol, vitamin E, trolox, citrate, and salts thereof. Preferably, the reducing agent is ascorbic acid, erythiorbate, N-acetylcysteine, dithiothreitol, citrate or a combination thereof. If employed in the composition, preferably the antioxidant is present in an amount of from about 0.0001% to 2% by weight of the composition. It is also contemplated that the reducing agent may be present in an amount of about 0.0001%, 0.0005%, 0.001%, 0.005%, 0.01%, 0.05%, 0.1%, 0.5%, 1%, 1.5%, 2% by weight or any range defined by any two of the values listed above. In an embodiment of the present invention, the antioxidant is citric acid and it is present in the composition in an amount of about 0.5% by weight.

The DNA coating composition may further comprise a denaturing agent. Examples of denaturing agents include, but are not limited to urea, dodecyl sulfate, guanidinium chloride, guanidinium thiocyanate, and the like. Alcohols may also be considered denaturing agents provided they are employed in an amount sufficient to denature one or more proteins, preferably one or more nucleases. The ability of a component to act as a denaturing agent may be performed using a variety of tests in the art.

The DNA coating composition may also comprise a fluorescent and/or a luminescent compound or dye to permit detection of the coating on an object. Without wishing to be limiting in any manner, any organic or inorganic compound that exhibits fluorescence or luminescence when excited with light, for example, but not limited to light in the ultraviolet to infra-red range of the light spectrum may be employed by the present invention. Preferably the compound exhibits a high quantum yield, as would be known in the art. Examples of fluorescent and/or luminescent compounds include, but are not limited to 1-naphthalenesulfonic acid, 1,5-naphthalenedisulfonic acid sodium salt, 1-napthol-4-sulfonic acid sodium salt, fluorescein isothiocyanate, 2,6 dichlorofluorescein, 4-amino-1-naphthalenesulfonic acid sodium salt, proidium iodide as well as water soluble fullerene derivatives. The present invention also contemplates employing quantum dots, for example, but not limited to nanocrystals of CdTe, CdSe, ZnSe, InP, InAs, and CdS, and also dendrimer-terminal functionalised compounds.

A variety of fluorescent and/or luminescent compounds that may be employed in the DNA coating composition are available from Molecular Probes Inc. However, the present invention is not meant to be limited to such fluorescent and/or luminescent compounds.

The concentration of the luminescent compound employed in the composition may vary depending on the extinction coefficient, quantum efficiency of the particular compound or dye, the excitation and emission wavelengths, and the detection method used to identify the luminescent compound. Generally, the luminescent compound or dye is preferably present in an amount ranging from about $1 \times 10^{-5}$ to about 5% by weight, preferably about $1 \times 10^{-4}$% to about 2% by weight, more preferably about $1 \times 10^{-3}$ to about 2% by weight of the composition. In alternate embodiments of the present invention, which are not meant to be limiting in any manner, the fluorescent and/or luminescent compound may be present in a wt % amount of about $1 \times 10^{-5}$, $5 \times 10^{-5}$, $1 \times 10^{-4}$, $5 \times 10^{-4}$, $1 \times 10^{-3}$, $5 \times 10^{-3}$, $1 \times 10^{-2}$, $5 \times 10^{-2}$, $1 \times 10^{-1}$, $5 \times 10^{-1}$, 1%, 1.5%, 2%, 3%, 4%, and 5% by weight, or any range defined by any of the values listed above. However, any amount that may be detected by the appropriate means, as would be evident to someone of skill in the art may be employed in the present invention.

The composition of the present invention as defined above may be customized, for example, but not limited to, by inclusion of one or more specific fluorescent and/or luminescent compounds. For example, but not wishing to be limiting in any manner, the excitation-detection wavelengths can be tailored to common/inexpensive detection procedure such as UV or visible illumination devices with visible detection, or more sophisticated/covert procedures such as narrow bandwidth illumination in the UV, visible or infrared portion of the electromagnetic spectrum, with specialized detection generally requiring narrow bandwidth detectors optimized for the particular emission signature of the dye or composition of dyes used. Another class of chemical compounds suited for this application is quantum dot conjugates. These compounds are nanometer scale particles that have unique optical properties. In one particular application that is contemplated by the present invention, quantum dot polymeric materials have been made with surfaces that are specific for DNA. A DNA coating solution containing quantum dots as an indicator "dye" may have the added benefit of being able to specifically bind to the DNA after its addition to the coating solution.

Although the use of a fluorescent and/or luminescent compound in the DNA coating composition greatly facilitates the identification of objects that have been marked by the composition, it is to be understood that the presence of a fluorescent or luminescent compound in the DNA coating solution is not required. The most covert means of application, is for the solution to be invisible and its location on an object to be carefully noted by the applicant or owner. This type of approach is preferred for marking rare and unique items. The information about the location of the mark may be known only by the owner who may optionally enter the information into a database, data structure or the like as is described herein.

The use of a UV absorbing compound does not necessarily preclude the use of dyes or compounds that are excited by UV light. The choice of the UV absorbing compound may depend on other components in the composition, for example a tracking dye that is also employed. For example, but without wishing to be limiting in any manner, a UV absorbing compound that absorbs light below about 350 nm may be employed with a dye that fluoresces in the visible range (400-700 nm) when excited with light having a peak wavelength between 350 and 400 nm.

It is also contemplated that the DNA coating composition may comprise an infrared absorbing compound or dye. Without wishing to be considered limiting or bound by theory in any manner, many IR dyes appear invisible when viewed by the unaided eye but can be seen as a dark or black spot when viewed using appropriate devices that can detect electromagnetic radiation between 700 nm and 1800 nm (such as the ccd detectors and the like).

The DNA coating composition may further comprise one or more buffering agents. Examples of buffering agents include, but are not limited to phosphate buffers as are known in the art, TRIS, HEPES, BES, carbonate buffers and the like. Preferably, the pH of the DNA coating composition is in the range of 7.0 to about 10.0, preferably about 8. The chemical backbone and the DNA purine bases is usually most stable at a slightly alkaline pH, with an optimal stability generally recognized as being within a pH range of about 7-11, and desirably a pH of about 8. Below a pH of about 6, depurination (i.e., spontaneous loss of purine bases from the deoxyribose-phosphate backbone) can occur. Above a pH of about 10, spontaneous loss of amino groups from cytosine nucleotides may occur, thereby converting cytosine to uracil. Above a pH of about 12, DNA may be denatured, converting it from the double-stranded form to the single-stranded form.

The DNA coating composition may also comprise one or more chelator compounds, for example, but not limited to divalent metal chelator compounds such as ethylenediaminetetraacetic acid (EDTA), [ethylenebis(oxyethylenenitrilo)] tetraacetic acid (EGTA), cyclohexane diaminetetraacetate (CDTA), and 1,2-bis(2-aminophenoxy)ethane-N,N,N',N'-tetraacetic acid (BAPTA), diethylenetriamine pentaacetic acid (DTPA), tetraazacyclododecanetetraacetic acid (DOTA), tetraazacyclotetradecanetetraacetic acid (TETA), desferrioximine or salts of any of those listed above.

The DNA coating composition may further comprise one or more preservatives and/or one or more biocidal agents. Examples of preservatives include for example, but are not limited to sodium azide, sodium salicilate, or a combination thereof. Examples of biocidal agents include, for example but are not limited to DOWICIL 75, POLYQUAD, or a combination thereof. However, any preservative and/or biocidal agent known in the art may be employed in the DNA coating composition. In an embodiment, which is not meant to be limiting in any manner, the preservative and/or biocidal agent is present in an amount ranging form about 0.00001% to about 1% by weight. However, its is contemplated that the preservative and/or biocidal agent may be present in an amount of about 0.0001%, 0.001%, 0.01%, 0.1%, 1% by weight or the preservative and/or biocidal agent may be present in a range defined by any two of the values listed above.

The DNA coating composition may further comprise a corrosion inhibitor. Example of corrosion inhibitors may include, but are not limited to a metal salt of an inorganic oxy-acid, for example, but not limited to zinc, magnesium, manganese, strontium or barium phosphate. A corrosion inhibitor may be employed under a variety of circumstances, for example, but not limited to when the DNA coating composition is applied to a metal object or in a region of an object wherein corrosion may be a concern. In an embodiment which is not meant to be limiting, the corrosion inhibitor may be present in an amount ranging from about 0.00005% to about 2% by weight. However, it is contemplated that the corrosion inhibitor may be present in an amount of about 0.00005%, 0.0001%, 0.001%, 0.01%, 0.1%, 1%, or 2% by weight or the preservative and/or biocidal agent may be present in a range defined by any two of the values listed above.

The composition may be applied to a surface or part of a surface on an object. It is to be understood that the DNA coating composition may not comprise DNA initially. For example, the DNA coating composition may be marketed, sold or the like free of DNA and the purchaser or user may add DNA as required. However, it is also contemplated that the DNA coating composition may comprise DNA from a subject. Thus, in a first embodiment, the DNA coating composition is free of DNA. In an alternate embodiment, the composition may comprise the DNA of a subject. It is also possible that the composition may comprise DNA from one or more subjects, for example, but not wishing to be limiting, to mark an item that is owned by a group of subjects. However, if an item is owned by a single individual, it may be preferable to mark the item or article with a DNA coating composition that comprises DNA from a single individual.

The DNA may be obtained from a subject by any method known in the art. For example, DNA may be obtained from cells in one or more body fluids or tissues of a subject as would be known in the art. In an embodiment of the present invention, the DNA is obtained from cells taken from the mouth of a subject. For example, DNA may be obtained from a subject by swabbing the inside of the subject's cheek with a suitable implement, for example, but not limited to a brush, swab or the like.

Once the cells containing DNA are isolated from a subject, they may be placed directly within the DNA coating composition. The components within the DNA coating composition may cause the cells to shrink, swell, or burst depending on the components contained therein. In an embodiment of the present invention, the cells and organelles contained therein are lysed, dissolved or the like and the DNA contained therein is released into the DNA coating composition. In an alternate embodiment, the DNA remains within the cells that are isolated from the subject.

It is to be appreciated that the inside of the mouth does not provide a sterile medium to obtain cells and thus it is preferred that cells isolated therefrom (or any other region or area of a subject) are processed quickly to ensure that DNA contained therein is not degraded.

In an alternate embodiment, which is not meant to be limiting in any manner, a buccal swab may be used to collect epithelial cells containing DNA from an individual, and subsequently, one or more drops of the DNA coating solution may be added to the swab in order to mark one or more items of interest.

In an alternate embodiment, that is not meant to be limiting in any manner, the DNA from a subject may be provided/obtained from a subject's saliva, as it has long been known that cellular DNA is present in saliva and that this DNA is suitable for forensic purposes (van Schie, et al., J. Immunol. Methods 208: 91-101, 1997; Terasaki, et al., Hum. Immunol. 59: 597-598, 1998) which are herein incorporated by reference).

The DNA coating composition preferably exhibits the following properties:

DNA contained in the DNA coating composition is protected from degradation after the composition is applied to an object, asset, article or the like. Preferably, the DNA is protected from being degraded for a period of at least about 6 months, more preferably about 1 year, more preferably about 2 years, still more preferably about 5 years, more preferably about 10 years, more preferably about 20 years, or longer. By the term "degraded" or "degradation" it is meant that the DNA comprises less than 50% cleavage of the DNA, more preferably less than about 30% cleavage, still more preferably less than about 20% cleavage, still more preferably less than about 10% cleavage, more preferably still less than about 1% cleavage of the original DNA contained in the composition. By the term "cleavage" it is meant either exonuclease cleavage, endonuclease cleavage or a combination thereof.

The DNA coating composition is stable over a time period of at least about 12 months, more preferably at least 24 months, still more preferably at least about 36 months.

The DNA coating composition can be applied as a liquid to a surface, but subsequently hardens, preferably into a substantially clear or opaque coating.

Any object that comprises a substantially solid surface may be marked with the DNA coating composition. For example DNA contained within the DNA coating composition may be used to mark ownership of objects. Examples of such object may include, but are not limited to paper goods, money, bank notes, bonds, cheques, security documents or any other printed matter, jewelry including but not limited to precious stones, rings, earrings, necklaces, watches and the like, works of art including but not limited to sculptures, paintings and the like; electronic goods, such as, but not limited to computers, computer peripheral devices, printers, microchips, disc drives, televisions, radios, DVD players, CD players, sound systems and the like; furniture, appliances, antiques, clothing, and other personal possessions, for example, but not limited to cameras, automobiles, bicycles, motorcycles and the like.

DNA may be recovered from an object marked with the DNA coating composition by a variety of methods as would be known in the art. For example, but not wishing to be limiting in any manner, the object may be wiped with a solvent, solution or combination thereof which is capable of dissolving the polymer of the DNA coating composition thereby providing access to DNA contained therein. For example, but not wishing to be considered limiting in any manner, DNA from a subject may be contained in a DNA coating composition that comprises an enamel which may be dissolved by a recovery solvent, for example, but not limited to ethyl acetate or the like. In this manner DNA may be removed from an object treated with the DNA coating composition.

It is also contemplated that a DNA coating composition comprising DNA may be removed from an object, for example, but not limited to gentle abrasion or mild scraping with an appropriate implement. Such implements may include but are not limited to a file, sand paper and the like.

The DNA recovered from an object may be extracted, washed, purified, concentrated, amplified or a combination thereof using well-known methods in the art. For example, the DNA may be subjected to one or more precipitations, extractions, centrifugations, filtrations, microfiltrations, chromatography separations, electrophoresis separations or a combination thereof. In addition, the DNA that is isolated may be subjected to one or more enzymatic reactions including, but not limited to any cloning step that would be known in the art, amplification steps such as but not limited to polymerase chain reaction (PCR) or the like.

In an embodiment of the present invention which is not meant to limit the invention in any way, the DNA isolated from an object treated with the DNA coating composition is purified and amplified by PCR or a similar procedure as would be known in the art. Once amplified, the DNA may be sequenced, subjected to restriction length fragment polymorphism, microsatelite, short tandem repeat (STR) analysis or the like as a means to provide information on the owner of the object. The sequence of the DNA, the restriction pattern, electropherogram or the like may be used to compare to a sample of DNA taken from one or more potential subjects. Also, the information may be used to search a database or datastructure to identify the owner of the object. Similarly, it may be possible to search a database or datastructure to identify objects that have been found or recovered by authorities, and subsequently process the object to remove DNA that may be contained thereon to confirm ownership of the object or article.

It is also contemplated that the DNA coating composition may be employed on or in personal identification documents, for example, but not limited to passports, driver's licenses, health cards, medicare cards, bank cards, credit cards, birth certificates and the like. DNA from the owner of the document may be applied to the document using the DNA coating composition. In the event that it is necessary to ascertain whether the document belongs to the person carrying it, DNA may be sampled from both the person carrying the document and the document itself to ensure they match.

The present invention also contemplates that the DNA coating compositions may be employed with forensic field devices such as DNA analyzers and the like as described in DNA Forensics: From RFLP to PCR-STR and Beyond, Phillip Jones, Fall 2004 Forensic Magazine which is herein incorporated by reference.

Methods of Marking Objections for Identification

The present invention also provides a method of treating an object with a DNA coating composition comprising,
 a) selecting a DNA coating composition;
 b) obtaining DNA from a subject;
 c) adding said DNA from a subject to the DNA coating composition to produce a DNA coating composition that comprises DNA;
 d) applying the DNA coating composition that comprises DNA to the object.

The present invention also provides a method of processing an object treated with a DNA coating composition comprising,
 a) obtaining an object treated with a DNA coating composition that comprises DNA;
 b) treating said DNA coating composition to remove DNA contained in the DNA coating composition;
 c) optionally purifying said DNA, and;
 d) subjecting said DNA to an amplification process, for example, but not limited to PCR or the like to produce amplified DNA, and analyzing the amplified DNA.

The amplified DNA may be analyzed by any suitable method known in the art, for example, but not limited to nucleotide sequencing, RFLP analysis, microsatellite analysis, DNA profiling, electrophoresis, for example, but not limited to capillary electrophoresis, or the like, or any combination thereof.

The method may optionally comprise the step of searching a database, or datastructure to identify a subject that matches the information obtained from step d) subjecting said amplified DNA to an amplification process. For example, but not wishing to be limiting in any manner, a subject may choose to register one or more nucleotide sequences of DNA contained within himself or herself so that ownership of found or recovered objects that comprise a DNA coating composition may be readily determined. In an alternate embodiment, a subject may choose to register his or her DNA profile using one or more known markers performed by, for example, but not limited to microsatellite analysis, short tandem repeat analysis or the like. In still another embodiment, the owner may choose to record or register only objects that have been treated with the DNA coating composition. In order to prove ownership, the subject may later furnish a biological sample that comprises DNA and the DNA from the subject may be compared to DNA only the found or recovered object.

The method of the present invention may also comprise a step of recording or registering objects that have been treated with a DNA coating composition (comprising DNA) into a database, data structure or the like which may be, but is not limited to being an electronic database. The electronic database may be online or off-line. In a preferred embodiment, the electronic database is online and information may be transmitted to the database via the internet. Without wishing to be limiting in any manner, in such an embodiment, a subject may be able to list and optionally describe objects that have been marked with the DNA coating composition. Information that may be recorded or registered include, but is not limited to a subject's name, address, telephone number, fax number, email address, list of objects marked, description of objects marked, location that objects have been marked, date object was purchased or acquired, place object was purchased or acquired, serial numbers or other identification numbers, contact information of person if an item matching the object is found, etc.

It is also contemplated that a user of a DNA marking composition may write down all of the objects that are marked with the DNA coating composition and this information may be transmitted to an individual or organization that subsequently enters the information into a database or data structure. If required, the user may also submit receipts of objects that have been purchased or the like to provide proof that the user is the owner of the object that has been marked with the DNA marking composition.

Kits

The present invention also provides a kit for marking objects with a DNA coating composition. The kit may comprise a DNA coating composition as described herein throughout, one or more implements for obtaining DNA from a biological fluid or tissue of the subject, instructions for obtaining DNA from the subject, one or more DNA sample archive pouches, a DNA coating composition applicator, for example a brush or the like, instructions for marking objects with the DNA coating composition, one or more forms that may be used to list items marked with the DNA coating composition of the present invention, a logon ID and password or unique identifier code or number for a system, database or data structure that allows a subject to record items that have been marked with the DNA coating composition into the database, or a combination thereof.

In an embodiment of the present invention which is not meant to be considered limiting in any manner, the unique registration code/number may provide the owner with private access to a secure web-based application, wherein individuals record or register information concerning their physical objects and assets treated with the DNA coating composition thereby linking an owner to its asset or physical property. The secure web based application may record information about the individual, for example, but not limited to the name or codename of the individual and the address as well as the answer to one or more generic questions about the individual.

Once the relevant information from the individual has been entered, it is preferred that the data is moved offline such that it is no longer accessible through the web application and would then transferred and held on a stand alone system. From this process, a subsequent registration number may be generated to allow the owner to register items that would have been marked with the DNA coating composition against that number in a secure database that may only be accessed and reviewed by registrants for their own record maintenance, and by recognized authorities which may have a need to link recovered assets marked with DNA coating composition to their potential owners. It would not be possible to determine the location of the assets from the registry. This would hinder anyone successful in gaining unauthorized access to the registry, to use it to identify the location of valuable assets. Authorities that have identified recovered items from the registry marked with the DNA coating composition may access the registry and place a request (online) that they be contacted by their owner by providing appropriate contact information. This request may then be passed on to the owner in a separate communication.

The process could also be accomplished by a hard copy and mail-in process for those individuals who don't have access to a computer.

The DNA coating composition may be provided in one or more containers, for example, but not limited to one or more vials, screw cap tubes, eppendorf tubes, or the like. It is also contemplated that the DNA coating composition may be provided as a single use container, that may be employed to mark one or more objects.

The compositions and methods as disclosed herein may be used for a variety of purposes, for example, but not wishing to be limiting in any manner, to protect an individual's assets in order to facilitate making a claim of ownership in the event such assets are lost or stolen.

DNA can be obtained from a variety of different sources. For example, but not to be considered limiting in any manner, the DNA of person can be obtained by collecting epithelial cells by swabbing the interior of their mouth. The collected cells may be incorporated into the DNA coating composition, which preserves and protects the DNA from degradation and environmental conditions. The DNA coating composition that comprises DNA may be considered a marking solution in that the solution can be applied on the surface of a wide variety of materials such as, but not limited to metals, plastics, glass, wood, paper, fabrics etc, using a small brush or applicator. Once dry, the object marked bears a hardened coating that comprises DNA of an individual. Asset tracking may be achieved by having knowledge of the location of the coating or for example, but not limited to, by detecting a fluorescent, luminescent or other marker contained in the solution using one or more lighting techniques known in the art. Alternate methods of detecting DNA on an object as would be known in the art may also be employed. The DNA may be sampled from the surface of the object in the event proof of ownership becomes necessary. Identification and analysis of the DNA may achieved using conventional methods, for example, but not limited to PCR, RFLP analysis, nucleotide sequencing or the like.

In an embodiment of the present invention, which is not meant to limit the invention in any manner, the DNA marker and identification of asset owners is only undertaken in the event that establishing asset ownership becomes necessary.

The present invention also contemplates a system for linking an object to an owner comprising, a database, datastructure or the like as defined herein, for example, but not limited to comprising information concerning an item owned by a subject, information concerning an item found or recovered, or a combination thereof, and;

a DNA coating composition or a kit comprising the DNA coating composition as defined herein.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1a

Sample DNA Coating Composition 1

| Component | % (by weight) |
| --- | --- |
| Methanol | 20.0% |
| Polyurethane | 12.0% |
| p-aminobenzoic acid | 2.5% |
| Manganese chloride (1M) | 2.0% |
| Fumed silica | 0.5% |
| Citric acid | 0.5% |
| 2,5-thiophenediylbis (5-ter-butyl-1,3-benzoxazole) | 0.15% |
| EDTA (0.1M) | 0.1% |
| Sodium azide | 0.05% |
| DOWICIL 75 | 0.01% |
| Deionised water | up to 100% |

Example 1b

Sample DNA Coating Composition 2

| Component | % (by weight) |
| --- | --- |
| Methanol | 15.0% |
| Polyurethane | 17.0% |
| p-aminobenzoic acid | 2.5% |
| Manganese chloride (1M) | 2.0% |
| Fumed silica | 0.5% |
| Citric acid | 0.5% |
| 1,5-naphthalenedisulfonic acid sodium salt | 0.15% |
| EDTA (0.1M) | 0.1% |
| Sodium azide | 0.05% |
| DOWICIL 75 | 0.01% |
| Deionised water | up to 100% |

Example 1c

Sample DNA Coating Composition 3

| Component | % (by weight) |
|---|---|
| Methanol | 10.0% |
| Polyurethane | 25.0% |
| p-aminobenzoic acid | 2.5% |
| Manganese chloride (1M) | 2.0% |
| Fumed silica | 0.5% |
| Citric acid | 0.5% |
| 1,5-naphthalenedisulfonic acid sodium salt | 0.15% |
| EDTA (0.1M) | 0.1% |
| Sodium azide | 0.05% |
| DOWICIL 75 | 0.01% |
| Deionised water | up to 100% |

Example 1d

Sample DNA Coating Composition 4

| Component | % (by weight) |
|---|---|
| Polyurethane | 25.0% |
| p-aminobenzoic acid | 2.5% |
| Manganese chloride (1M) | 2.0% |
| Citric acid | 0.5% |
| 1,5-naphthalenedisulfonic acid sodium salt | 0.15% |
| EDTA (0.1M) | 0.1% |
| Sodium azide | 0.05% |
| DOWICIL 75 | 0.01% |
| Deionised water | up to 100% |

Example 1e

Sample DNA Coating Composition 5

| Component | % (by weight) |
|---|---|
| Polyurethane | 20.0% |
| p-aminobenzoic acid | 2.5% |
| Manganese chloride (1M) | 2.0% |
| Citric acid | 0.5% |
| 1,5-naphthalenedisulfonic acid sodium salt | 0.15% |
| EDTA (0.1M) | 0.1% |
| Sodium azide | 0.05% |
| DOWICIL 75 | 0.01% |
| Deionised water | up to 100% |

The present invention also contemplates a DNA coating composition as provided above wherein deionised water is present in an amount of between about 40% to about 80% (w/w), methanol is present in an amount of about 0% to about 20%, polyurethane is present in an amount of about 10 to about 40% (w/w), or any combination thereof.

Example 1f

Sample DNA Coating Composition 6

| Component | % (by weight) |
|---|---|
| Acrylic polymer | 40.0% |
| p-aminobenzoic acid | 2.5% |
| Manganese chloride (1M) | 2.0% |
| Citric acid | 0.5% |
| 1,5-naphthalenedisulfonic acid sodium salt | 0.5% |
| EDTA (0.1M) | 0.1% |
| Sodium azide | 0.05% |
| POLYQUAD | 0.01% |
| Deionised water | up to 100% |

Example 1g

Sample DNA Coating Composition 7

| Component | % (by weight) |
|---|---|
| Acrylic polymer | 34.0% |
| Manganese chloride (1M) | 2.0% |
| Citric acid | 0.5% |
| 1,5-naphthalenedisulfonic acid sodium salt | 0.5% |
| EDTA (0.1M) | 0.1% |
| Sodium azide | 0.05% |
| POLYQUAD | 0.01% |
| Deionised water | up to 100% |

Example 1h

Sample DNA Coating Composition 8

| Component | % (by weight) |
|---|---|
| Acrylic polymer (polymethyl methacrylate) | 35.0% |
| Deionised water | 65.0% |

Example 1i

Sample DNA Coating Composition 9

| Component | % (by weight) |
|---|---|
| Acrylic polymer (polymethyl methacrylate) | 25.0% |
| Deionised water | 75.0% |

The present invention also contemplates DNA coating compositions as defined above wherein the acrylic polymer is present in an amount of from about 10% to about 60% (w/w), more preferably about 10% to about 50% (w/w), still more preferably about 20% to about 40% (w/w).

Example 2

To make the DNA coating composition a unique marking solution, the DNA from one or more individuals is added to the composition. This may be performed by adding epithelial cells that have been freshly sampled from the mouth. Preferably, this is done in the morning before eating or drinking. Using an appropriate cell sampling tool, for example, one that may be provided with a kit, the inside of each cheek is rubbed or gently scrapped about three to six times, or for about 20 to 60 seconds. The tip of the tool is then soaked in the DNA coating composition bottle for about 5 minutes. The DNA coating composition solution is a coating solution which, once combined with a person's DNA, becomes a unique marking liquid that can be used to mark an object, for example, but not limited to a person's possessions or assets. Marking of objects may be performed using a fine paint brush. The DNA coating composition comprising DNA of a owner may be applied to an object in one or more areas that are not commonly touched when the object is handled. Without wishing to be considered limiting in any manner, a suitable amount of DNA coating composition ranging from one quarter to one half the area of a small fingernail (generally about $0.1$ $cm^2$ to about $1$ $cm^2$) may be applied to objects to mark them with an owner's DNA. The DNA coating composition may be applied over areas outside the range noted above, as would be evident to a person of skill in the art.

To mark an object with the DNA coating composition solution, the procedure below can be followed;

The DNA coating composition solution is shaken vigorously for about 2 minutes before use.

Mark objects by applying between about one to about three 1 cm strokes of the brush-comprising the DNA coating composition comprising DNA, preferably the same amount that would be required to cover about half a fingernail, to discrete areas, preferably away from the main face of the object. For example, it is preferred to mark the back of a painting, the underside, backside (or inside if possible) of consumer or electronic devices and office equipment, etc. The inside of vehicles can be marked in a number of different areas such as in various compartments, under seats, etc. It is preferable to avoid marking objects in areas most likely to be touched when items are being used, handled or transported. Items that are for exterior use should be marked in areas that provide some degree of protection from environmental conditions such as direct exposure to sunlight, continuous exposure to water, snow, salt, or a combination thereof.

The individual that marks an object preferably makes a note and records where the items are marked. The location of a mark may be entered into a database system or a data structure. In an embodiment, the location of a mark on an object may be entered into a secure web based or internet site.

Items marked with the DNA coating composition solution with a fluorescent, luminescent or other tag are preferably marked in areas that can be readily detected upon inspection by authorities.

Items marked with the DNA coating composition solution without a fluorescent, luminescent or other tag may be marked in concealed areas that can later be disclosed to authorities for potential sampling.

(1) To register with the DNA coating composition DNA coating composition Product-registry website, a customer will navigate with their web browser to the appropriate section on the DNA coating composition product-registry website, and enter a unique LoginID and Password from the DNA coating composition marking kit.

(2) At this point, the customer may be prompted to change both their LoginID and Password.

(3) The customer will then be prompted to enter contact information, so that when a Product is stolen/lost and subsequently recovered, the customer can be contacted. The contact information is optional.

(4) At this point, the customer is registered and can then begin entering objects/products/assets in the system that they have marked with their DNA coating composition marking kit.

(5) For each product the customer enters on the DNA coating composition product-registry website, they can also indicate where the product has been marked by the DNA coating composition marking kit. This marking location can be indicated on the DNA coating composition marking kit product card.

Police Website Registration
  Members of police forces can register on the DNA coating composition product registry website
  A Police organization must be registered prior to any members registering on the DNA coating composition product-registry website.
  The Police organization will be provided with LoginIDs and Password for their members.
  1) To register with the DNA coating composition product-registry website, a Police officer will navigate with their web browser to the appropriate section on the DNA coating composition product-registry website, and enter a unique LoginID and Password, as well as their email address and telephone number.
  2) At this point, the Police officer may then be prompted to change both their LoginID and Password.
  3) Once registered, the Police officer can search a stolen and/or lost product list maintained by the system.
  Product Listing
  A customer may view, add, update, and delete their own products/assets/objects on the DNA coating composition product-registry website.
  Product Stolen
  When a DNA coating composition customer has a product/asset/object stolen or lost, they can record the event in the DNA coating composition product-registry website that this product has been stolen/lost.
  Customer Profile
  A Customer may change at any time their Login ID, Password, and contact information, on the DNA coating composition product registry web-site
  Product Recovery
  (1) A stolen/lost product/asset/object is recovered by the Police. The item(s) that have been marked with DNA coating composition that comprise a fluorescent/luminescent dye can be detected by examining the item with the appropriate excitation source (UV, IR, etc.)
  (2) The Police can search the DNA coating composition product-registry website for a matching products/assets/objects; preferably only Product Identification numbers and descriptions are visible to the Police.
  (3) If one or more matches are found, the Police can contact the organization responsible for providing DNA coating composition and maintaining the database systems via a web form; this will identify to DNA coating composition the Customer associated with the stolen/lost product, as well as the Police officer who contacted the organization.
  (4a) If contact information is available for the customer associated with the stolen/lost product, the DNA coating composition organization will contact them, and provide them with contact information of the Police officer who contacted the DNA coating composition.

(4b) If contact information is not available for the customer associated with the stolen/lost product, the next time the customer logs onto the DNA coating composition product-registry website, they will be provided with a message indicating that their product may have been recovered, as well as the contact information of the Police officer who contacted the organization or individual providing the DNA coating composition and product registry website.

(5) Once the customer and Police are in contact, the Police may ask the customer to identify where on the product the customer has placed their DNA marking (6) If required, the Customer may be required to provide the Police with DNA sample from the DNA coating composition marking kit, to match with that on the product (7) If the customer has recovered the product, they can indicate on the DNA coating composition product-registry website that the product has been recovered, so that it will not display on the stolen/lost product list available to the Police.

Example 3

Processing and Data Analysis of DNA Obtained from DNA Coating Compositions

DNA Extraction

DNA was extracted from DNA coating composition containing cheek cells using the DNeasy™ Tissue Kit (Qiagen).

1. Transfer 200 µL DNA coating composition comprising cells into a new 1.5 mL centrifuge tube.
2. Add 200 µL Buffer ATL and 25 µL 20 mg/mL Proteinase K to the sample.
3. Incubate sample at 70° C. for 10 min.
4. Add 200 µL 95-100% ethanol to the sample, and mix thoroughly by vortexing.
5. Pipet all mixture from step 4 (including any precipitate) into the DNeasy™ spin column sitting in a 2-mL collection tube. Centrifuge at 13,000 rpm for 1 minute (IEC MicroMB Centrifuge, International Equipment Company). Discard flow-through and collection tube in container designated for biohazardous waste.
6. Place the spin column in a new 2-mL collection tube, add 500 µL Buffer AW1, and centrifuge for 1 minute at 13,000 rpm (IEC MicroMB Centrifuge, International Equipment Company). Discard flow-through and collection tube in container designated for biohazardous waste.
7. Place the spin column in a new 2-mL collection tube, add 500 µL Buffer AW2 and centrifuge for 3 minutes at 13,000 rpm (IEC MicroMB Centrifuge, International Equipment Company) to dry the DNeasy™ membrane. Discard flow-through and collection tube in container designated for biohazardous waste.
8. Place the spin column in a clean 1.5-mL microcentrifuge tube, and pipet 50 µL pre-warmed (70° C.) Buffer AE directly onto the membrane. Incubate at room temperature for 1 minute, and then elute DNA solution by centrifugation for 1 minute at 13,000 rpm (IEC MicroMB Centrifuge, International Equipment Company).
9. Discard spin column and quantify DNA.

DNA Amplification and Data Analysis

The following procedure is adapted from the User's manual of the AmpFISTR® Profiler Plus™ PCR Amplification Kit.

1. Add 10 µL DNA sample (about 0.125 ng/µL) to the PCR tube labeled with matching unique identification number.
2. Prepare mastermix as follow:
10. 50 µL of AmpFISTR® PCR Reaction Mix per sample
0.50 µL of AmpliTaq Gold® DNA Polymerase per sample
5.50 µL of AmpFISTR® Profiler Plus™ Primer Set per sample
3. For positive control, add 10 µL of AmpFISTR® Control DNA 9947
4. For negative control, add 10 µL of AE buffer to the labeled Negative Control Tube.
5. Place the PCR tubes in the GeneAmp® PCR Thermal Cycler for PCR reaction as described in Profiler manual.
6. PCR products are run on 36-cm well-to-read plates on the ABI Prism® 377 DNA Sequencer DNA data is analyzed using GeneScan® Analysis 3.1 software and Genotyper® Analysis 2.5 Software.

Testing a Sample DNA Coating Composition

Figure 1:
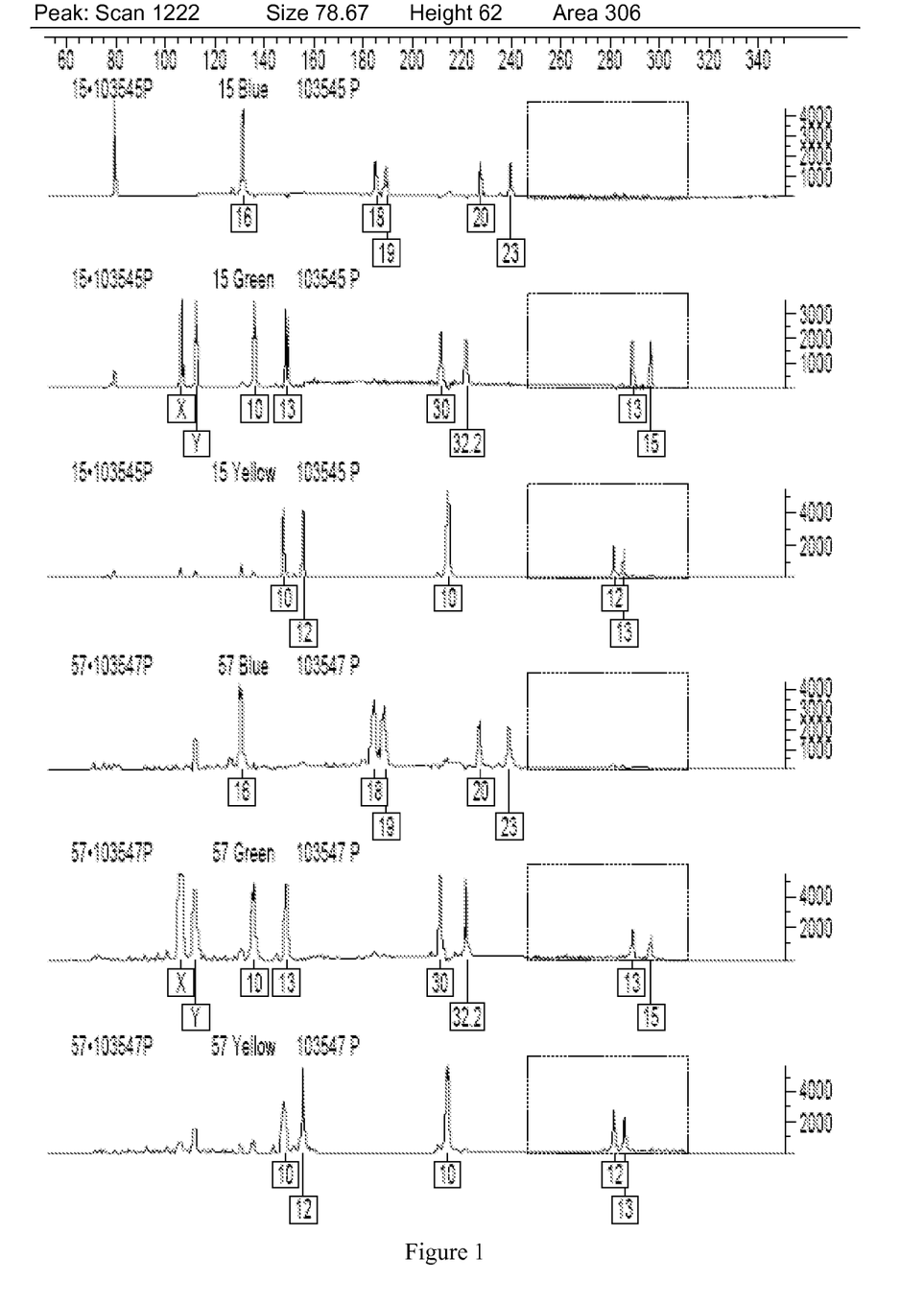
FIG. 1 shows electropherogram results following PCR amplification of DNA from a swab of cells (103545) compared to that obtained after the cells were placed in a DNA coating composition (103547 (Example 1i DNA Coating composition 9)). The electropherogram profiles shown in FIG. 1 indicate that the same DNA sample is present on the swab and in the DNA coating composition.

The DNA profiles from a swab of cells (103545) was compared to that obtained after the cells were placed in a DNA coating composition (103547 (Example 1i DNA Coating composition 9)). The results are shown in Table 1 and FIG. 1. The electropherogram profiles shown in FIG. 1 indicate that the same DNA sample is present on the swab and in the DNA coating composition.

TABLE 1

Markers used in profiling DNA obtained from cheek swab (103545) versus DNA coating composition (103547 (Example 1i DNA Coating composition 9)) comprising cells of the same individual.

| DNA MARKER | Cheek swab (103545) | Cells Coating Comp (103547) |
| --- | --- | --- |
| D13S317(13q22-31) | 10 | 10 |
| D18S51(18q21.3) | 13, 15 | 13, 15 |
| D21S11(21) | 30, 32.2 | 30, 32.2 |
| D3S1358(3p) | 16 | 16 |
| D5S818(5q21-31) | 10, 12 | 10, 12 |
| D7S820(7q11.21-22) | 12, 13 | 12, 13 |
| D8S1179(8) | 10, 13 | 10, 13 |
| FGA(4q28) | 20, 23 | 20, 23 |
| vWA(12p12-pter) | 18, 19 | 18, 19 |

Example 4

DNA Recovery from Hard Surfaces

1. DNA from a subject was sampled using a buccal swab and a few drops of the DNA coating composition (Example 1g; sample DNA coating 7) was added directly to the swab.
2. Applied DNA coating composition comprising DNA to two different objects. The DNA coating composition comprising DNA was applied to an area covering about 2 cm². The objects included:
   a. Plastic
   b. Shiny Metal DNA was sampled separately from the objects using a swab moistened with water. The swabs were subjected to the following protocol:

Perform Phenol Chloroform extraction on all swabs for all surfaces a. Add 200 µL of ATL and 25 µL of Proteinase K to the solution in the centrifuge tube. Vortex.
b. Incubated in shaking incubator for >1 hour at 56° C.
c. Add 500 µL of Phenol Chloroform to each tube.
d. Placed on rocker for 6 minutes. Centrifuged for 10 min at 13,000 rpm.
e. Transferred top layer into a new, labeled 1.5 mL centrifuge tube.
f. Add 45 µL of Ammonium Acetate and 900 µL of 95% Ethanol.
g. Incubate at −20° C. overnight.

h. Centrifuged for 5 min at 13,000 rpm. Being careful not to disturb the pellet, the supernatant was discarded.

i. 500 μL of 70% ethanol was added and centrifuged for 5 min at 13,000 rpm.

j. The supernatant was discarded and the pellet was left to dry for 30 min. 50 μL of autoclaved IV water was added to the tubes.

DNA Profiling Results

Figure 2:
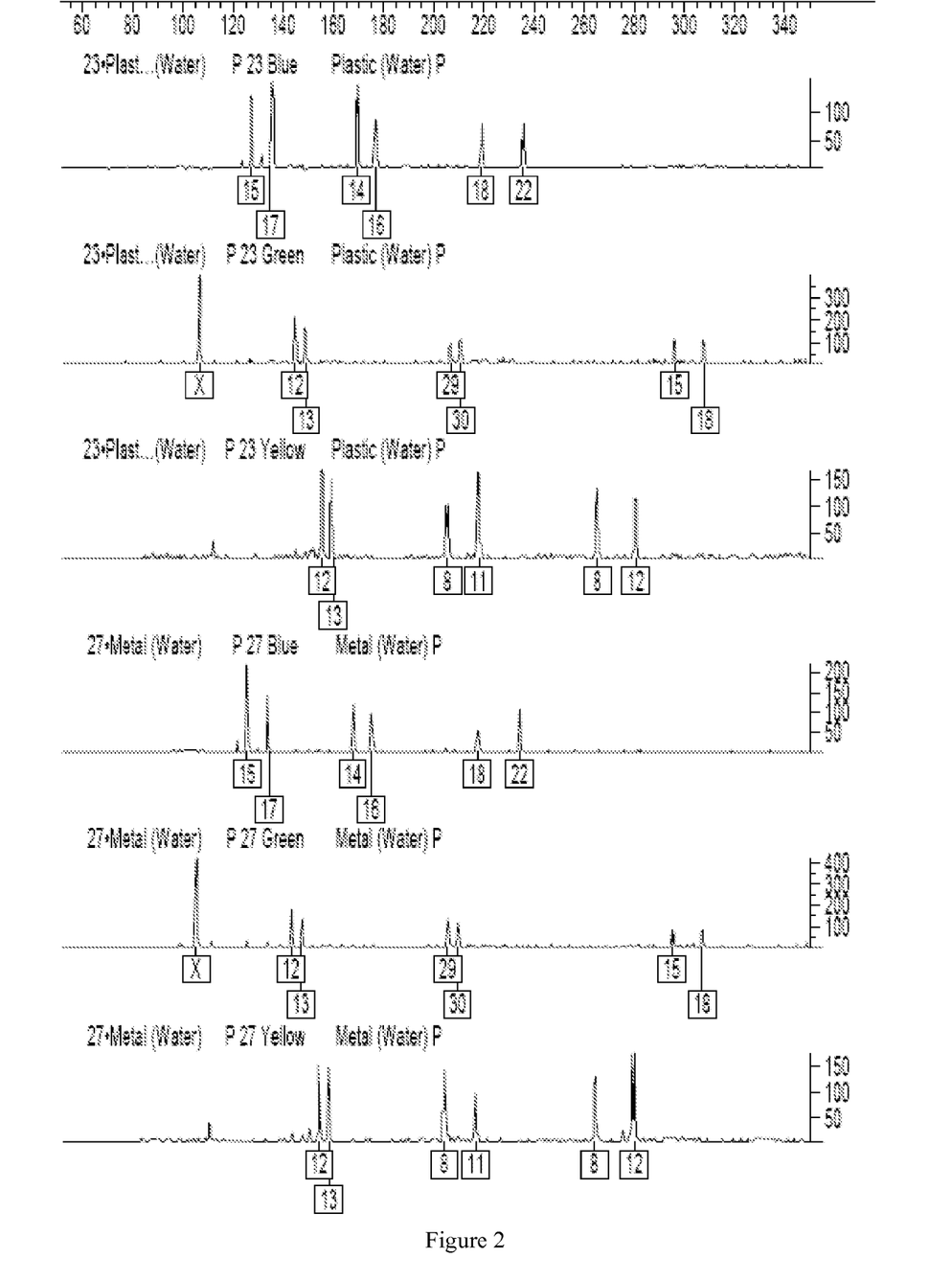
FIG. 2 shows electropherogram results obtained following PCR amplification of DNA after extraction of the DNA from objects having metal or plastic surfaces treated with a DNA coating composition comprising the DNA.

The plastic object produced a good full profile having an average signal of 150 RFU. The shiny metal surface also produced a good full profile having an average signal of 150 RFU. FIG. 2 shows the electropherograms obtained from the analysis of DNA sampled from objects having metal and plastic surfaces.

All citations are herein incorporated by reference.

The present invention has been described with regard to preferred embodiments. However, it will be obvious to persons skilled in the art that a number of variations and modifications can be made without departing from the scope of the invention as described herein.

The embodiment of the invention in which an exclusive property of privilege is claimed are defined as followed:

1. A composition for coating DNA comprising,
   a) one or more polymer compounds;
   b) water;
   c) manganese chloride;
   d) p-aminobenzoic acid, and
   e) one or more non-water polar solvents, wherein said one or more polymer compounds comprise polyurethane or acrylic polymer, said one or more non-water polar solvents comprise methanol, said composition further comprises silica, or said composition further comprises a luminescent compound.

2. The composition of claim 1, wherein said composition additionally comprises one or more dispersants, curing agents, catalysts, preservatives, thickeners, fillers, biocidal agents, buffering agents, luminescent compounds or dyes, antioxidants and/or reducing agents, detergents and/or denaturing agents, salts, light absorbing compounds, chelating agents, corrosion inhibitors, film forming components, plasticizers, adhesion promoters or a combination thereof.

3. The composition of claim 1, further comprising a DNA nucleotide sequence.

4. A composition comprising:

| | |
|---|---|
| Methanol | 20.0% |
| Polyurethane | 12.0% |
| p-aminobenzoic acid | 2.5% |
| Manganese chloride (1M) | 2.0% |
| Fumed silica | 0.5% |
| Citric acid | 0.5% |
| 2,5-thiophenediylbis (5-ter-butyl-1,3-benzoxazole) | 0.15% |
| EDTA (0.1M) | 0.1% |
| Sodium azide | 0.05% |
| 1-(3-chloroallyl)-3,5,7-triaza-1-azoniaadamantane chloride | 0.01% |
| Deionised water | up to 100% (all w/w). |

5. A method of treating an object with the composition according to claim 1 which comprises comprising,
   a) obtaining DNA from a subject;
   b) adding said DNA from a subject to the composition according to claim 1 to produce a DNA coating composition that comprises the DNA and treating the object with DNA coating composition.

6. The method of claim 5 which further comprises,
   c) treating said DNA coating composition to remove the DNA contained in the DNA coating composition;
   d) optionally purifying said DNA, and;
   e) subjecting said DNA to an amplification process to produce amplified DNA and analyzing said amplified DNA.

7. The method of claim 5, which further comprises at least one step of
   c) searching a database
   d) entering into a database one or more objects treated with the DNA coating composition, or
   e) a combination thereof.

8. A kit comprising the composition of claim 1.

9. The kit of claim 8, further comprising at least one of: one or more implements or obtaining DNA from a biological fluid or tissue of a subject, instructions for obtaining DNA from the subject, one or more sample DNA archive pouches, a DNA coating composition applicator, instructions for marking objects, one or more forms to list marked items, a log-on ID, password or unique identifier code, one or more containers, instructions for searching a website, instructions for submitting information to a website about objects that have been marked, or a combination thereof.

10. A system for linking an object to an owner comprising,
    a database comprising information concerning an item owned by a subject, information concerning an item found or recovered, or a combination thereof, and;
    a composition for coating DNA which comprises:
    a) one or more polymer compounds;
    b) water;
    c) manganese chloride;
    d) p-aminobenzoic acid, and
    e) one or more non-water polar solvents or a kit comprising the composition.

11. The method of claim 6, which further comprises at least one step of
    f) searching a database
    g) entering into a database one or more objects treated with the DNA coating composition, or
    h) a combination thereof.

12. A kit comprising the composition of claim 4.

13. The kit of claim 12, further comprising at least one of one or more implements or obtaining DNA from a biological fluid or tissue of a subject, instructions for obtaining DNA from the subject, one or more sample DNA archive pouches, a DNA coating composition applicator, instructions for marking objects, one or more forms to list marked items, a log-on ID, password or unique identifier code, one or more containers, instructions for searching a website, instructions for submitting information to a website about objects that have been marked, or a combination thereof.

14. A system for linking an object to an owner comprising,
    a database comprising information concerning an item owned by a subject, information concerning an item found or recovered, or a combination thereof, and;
    the composition of claim 1 or a kit comprising the composition of claim 1.

15. A system for linking an object to an owner comprising,
    a database comprising information concerning an item owned by a subject, information concerning an item found or recovered, or a combination thereof, and;
    the composition of claim 4 or a kit comprising the composition of claim 4.

16. A method of treating an object with the composition according to claim 4 which comprises
   a) obtaining DNA from a subject;
   b) adding said DNA from a subject to the composition according to claim 4 to produce a DNA coating composition that comprises the DNA and treating the object with DNA coating composition.

17. The method of claim 16, which further comprises,
   c) treating said DNA coating composition to remove the DNA contained in the DNA coating composition;
   d) optionally purifying said DNA, and;
   e) subjecting said DNA to an amplification process to produce amplified DNA and analyzing said amplified DNA.

18. The method of claim 16, which further comprises at least one step of
   c) searching a database
   d) entering into a database one or more objects treated with the DNA coating composition, or
   e) a combination thereof.

19. The method of claim 17, which further comprises at least one step of
   f) searching a database
   g) entering into a database one or more objects treated with the DNA coating composition, or
   h) a combination thereof.

20. The composition according to claim 1, wherein said composition comprises
   a)

| | |
|---|---|
| Methanol | 20.0% |
| Polyurethane | 12.0% |
| p-aminobenzoic acid | 2.5% |
| Manganese chloride (1M) | 2.0% |
| Fumed silica | 0.5% |
| Citric acid | 0.5% |
| 2,5-thiophenediylbis (5-ter-butyl-1,3-benzoxazole) | 0.15% |
| EDTA (0.1M) | 0.1% |
| Sodium azide | 0.05% |
| 1-(3-chloroallyl)-3,5,7-triaza-1-azoniaadamantane chloride | 0.01% |
| Deionised water | up to 100% (all w/w) | or
   b)

| | |
|---|---|
| Methanol | 15.0% |
| Polyurethane | 17.0% |
| p-aminobenzoic acid | 2.5% |
| Manganese chloride (1M) | 2.0% |
| Fumed silica | 0.5% |
| Citric acid | 0.5% |
| 1,5-naphthalenedisulfonic acid sodium salt | 0.15% |
| EDTA (0.1M) | 0.1% |
| Sodium azide | 0.05% |
| 1-(3-chloroallyl)-3,5,7-triaza-1-azoniaadamantane chloride | 0.01% |
| Deionised water | up to 100% (all w/w) | or
   c)

| | |
|---|---|
| Methanol | 10.0% |
| Polyurethane | 25.0% |
| p-aminobenzoic acid | 2.5% |
| Manganese chloride (1M) | 2.0% |
| Fumed silica | 0.5% |
| Citric acid | 0.5% |
| 1,5-naphthalenedisulfonic acid sodium salt | 0.15% |
| EDTA (0.1M) | 0.1% |
| Sodium azide | 0.05% |
| 1-(3-chloroallyl)-3,5,7-triaza-1-azoniaadamantane chloride | 0.01% |
| Deionised water | up to 100% (all w/w). |

* * * * *